United States Patent [19]

Martin

[11] Patent Number: 4,631,061
[45] Date of Patent: Dec. 23, 1986

[54] AUTOMATIC URINE DETECTING, COLLECTING AND STORING DEVICE

[76] Inventor: Frank D. Martin, P.O. Box 72, Kerrville, Tex. 78028

[21] Appl. No.: 622,117

[22] Filed: Jun. 19, 1984

[51] Int. Cl.⁴ .............................................. A61M 1/00
[52] U.S. Cl. ..................................... 604/318; 128/761; 128/765; 604/321; 604/323; 604/327; 604/329; 604/331; 4/301
[58] Field of Search ............... 604/317, 318, 320, 321, 604/322, 323, 324, 325, 326, 327, 328, 329, 330, 331; 128/138 A, 760–761, 765–766; 4/301, 313, 314, 316, 144.1, 144.2, 144.4, 144.3, DIG. 3

[56] References Cited

U.S. PATENT DOCUMENTS

| | | | |
|---|---|---|---|
| 2,649,591 | 8/1953 | McRae | 4/313 |
| 3,776,231 | 12/1973 | Holbrook et al. | 604/322 |
| 3,964,111 | 6/1976 | Packer | 4/144.4 |
| 4,117,845 | 10/1978 | Brown | 128/295 |
| 4,163,449 | 8/1979 | Regal | 128/138 A |
| 4,191,950 | 3/1980 | Levin et al. | 128/138 A X |
| 4,200,102 | 4/1980 | Duhamel et al. | 604/311 |
| 4,202,058 | 5/1980 | Anderson | 604/347 X |
| 4,212,295 | 7/1980 | Snyder | 128/138 A |
| 4,214,324 | 7/1980 | Kemper et al. | 4/314 X |
| 4,228,798 | 10/1980 | Deaton | 604/320 X |
| 4,270,231 | 6/1981 | Zint | 4/144.1 |
| 4,278,018 | 3/1981 | Alexander et al. | 128/760 X |
| 4,306,558 | 12/1981 | Kurtz et al. | 604/320 X |
| 4,343,342 | 8/1982 | Saito | 4/301 |
| 4,345,341 | 8/1982 | Saito | 4/301 |
| 4,360,933 | 11/1982 | Kimura et al. | 4/301 |
| 4,366,818 | 1/1983 | Izumi | 604/350 |
| 4,444,548 | 4/1984 | Andersen et al. | 604/317 X |

FOREIGN PATENT DOCUMENTS

| | | | |
|---|---|---|---|
| 0794640 | 9/1968 | Canada | 604/329 |
| 2107190 | 4/1983 | United Kingdom | 604/329 |

Primary Examiner—John F. Niebling
Assistant Examiner—Nam X. Nguyen
Attorney, Agent, or Firm—Donald W. Meeker

[57] ABSTRACT

A shallow collection vessel with liquid sensors and a resilient lip allows air around the genital-urinary area when not activated. Liquid urine in the vessel causes the sensors to activate a vacuum pump drawing the lip against the body of the user for a liquid tight seal and pumping the urine from the vessel through a tube and one-way valve to a temporary storage tank. Close and random spacing of the sensors creates a very sensitive device activated when the device is in any spacial orientation which might cause urine to contact the body by a minimal amount of urine, effecting the vacuum pump to remain active evaporating the urine within the vessel until the vessel is substantially dry. Paired electrical contacts or paired fibre optic elements are alternate liquid sensor means. Liquid level indicators within the tank signal a desired level for emptying and cause the pump to shut off upon reaching a dangerously full level. A condensation collecting trap keeps liquid out of the pump. A charcoal filter prevents urine odor from entering the atmosphere and reduces the vacuum pump noise exiting to the outside. A quick release valve is used to empty the tank. Working elements are housed in a sound insulated enclosure, which may be a simulated carrying case or backpack for ease of mobility. Variable self-contained and remote D.C. and A.C. power sources are used.

17 Claims, 10 Drawing Figures

AUTOMATIC URINE DETECTING, COLLECTING AND STORING DEVICE

BACKGROUND OF THE INVENTION

1. Technical Field

The present invention relates to urinary incontinence devices and in particular to a urine detecting, collecting and storing device with an automatic sensing control means for maintaining relative dryness adjacent to the body of the user by providing a vacuum pump which both pumps and evaporates the urine from the collection means.

2. Background Art

Urinary incontinence is a serious problem afflicting millions of people with a wide variety of ailments causing the problem. Embarrassment, discomfort, unhealthy skin conditions, infections and immobilization are some of the consequences of the problems. Babies and urinary incontinent adults suffer many of the same problems and require the same constant attention in monitoring and changing the means for dealing with the uncontrolled wetness.

None of the present methods of dealing with the problem are effective in removing the wetness by an automatic means not requiring constant attention. Incontinent pads and diapers, even those with wicking properties, all leave too much wetness on the skin of the wearer causing discomfort, irritation and rashes or worse if left unattended for long periods of time.

Urine collection devices typically leak from around the edges onto the wearer, and generally poor drainage characteristics leave a certain amount of urine in contact with the skin of the wearer.

Collection devices which are inserted into the urinary tract cause irriation and a constant threat of serious urinary infection. Devices secured on genital or adjacent skin tissue with an adhesive also cause serious skin irritation.

Devices, such as condumtype collectors, which prevent air from contacting the skin and hold in wetness cause rashes and other unpleasant skin conditions.

Urine collection devices are prone to overfilling and backing up on the wearer to cause a serious wetness problem.

Most other methods have a problem with urine odor.

DISCLOSURE OF INVENTION

By providing a vacuum which operates automatically upon sensing a very small amount of liquid and which stays in operation until there is a substantially dry condition in the urine collection vessel, wetness is eliminated from contact with the skin of the wearer. A series of wetness detecting sensors cover the interior of the collection vessel, and each sensor element is closely spaced to the neighboring element so that even a small amount of liquid, enough to span distance between the closely spaced sensors, activates the vacuum pump and keeps the pump activated after the bulk of the liquid is removed so that the vacuum pump serves as an evaporating means as well as a pumping means to dry out the collecting vessel and the skin of the wearer.

A resilient rubberized lip elevated above the surface of the collection vessel around the edge of the collecting well of the vessel serves as a liquid tight valve against the body of the wearer when the vacuum activates to draw the lip tightly against the user. Since the vacuum pump activates immediately upon contact by the first little quantity of urine and the vacuum does not stop until the urine is substantially pumped out and evaporated, leakage is prevented because when the liquid urine is in the vessel, the vacuum pump creates a tight seal.

A generally loose fitting collection vessel held in place by underwear, suspenders, a belt around the waist and crotch of the user or other supporting means allows some passage of air into the vessel when no liquid is present, thereby maintaining the skin in good condition with no adhesives or air tight coverings except when needed as the liquid begins to enter the vessel, and remaining air tight until the liquid is removed and substantially evaporated.

Safety sensing devices on the storage tank activate a light and buzzer or bell when the level in the tank reaches a preset level (such as 75-80% full) to notify the user or others in attendance that the storage tank should be emptied, and deactivate the vacuum pump when the level reaches a different preset value(such as 90%). Tank overflow is thereby prevented. Backflow into the collection vessel from the tank is prevented by a one-way valve or valves.

Urine odor is prevented from passing into the surrounding atmosphere by a filter between the vacuum pump and an outside exhaust. In addition the filter serves to cut down the exhaust noise from the vacuum pump.

BRIEF DESCRIPTION OF THE DRAWINGS

These and other details and advantages of my invention will be described in connection with the accompanying drawings, which are furnished only by way of illustration and not in limitation of the invention, and in which drawings.

BEST MODE FOR CARRYING OUT THE INVENTION

Figure 1:
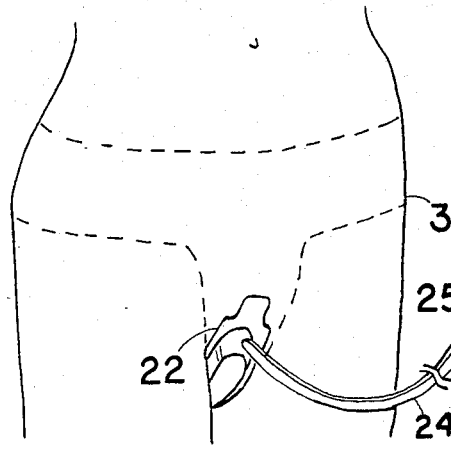
FIG. 1 is a schematic view in partial section showing the collection vessel in place on the user and the internal working mechanisms of the other components.
Figure 1:
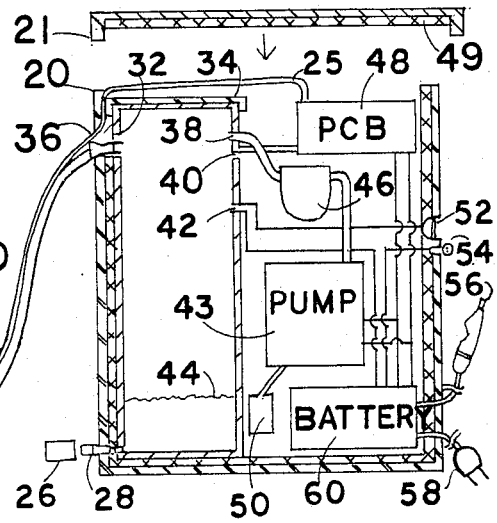
Figure 2:
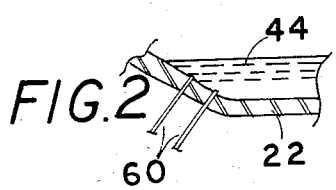
FIG. 2 is a partial sectional view taken through 2—2 of FIG. 8 showing a pair of liquid sensors through the well wall of the vessel.
Figure 4:
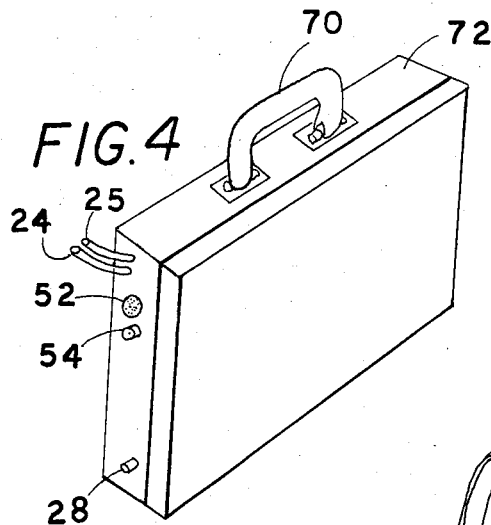
FIG. 4 is a perspective view showing a carrying case enclosure for the working components of the invention.
Figure 7:
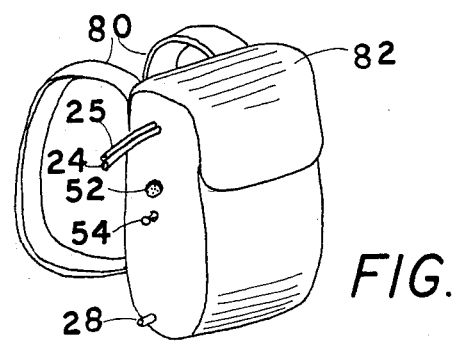
FIG. 7 is a perspective view showing a back pack enclosure for the working components of the invention.

In FIG. 1 a urine collection vessel 22 is held against the genital-urinary area of a user by any of a variety of means including regular underwear, suspenders or an elasticised belt 30 around the waist and crotch of the user, such as a belt used for feminine hygiene devices or a male athletic supporter. A flexible tube 24 leads from the collection vessel 22 to a temporary storage tank 32 cased in an enclosure 20 separate from the collection vessel. Insulation 49 inside the enclosure serves to quiet the noise produced by the vacuum pump 43 within the enclosure. A molded pastic enclosure 20 provides an inexpensive and easily maintained enclosure. Alternately the working components of the invention may be enclosed in a simulated standard carrying case, such as a brief case 72 with a handle 70, as indicated in FIG. 4, or a backpack 82 with shoulder straps 80, as in FIG. 7. Both provide an inconspicuous easy-to-carry means of enclosure.

Figure 8:
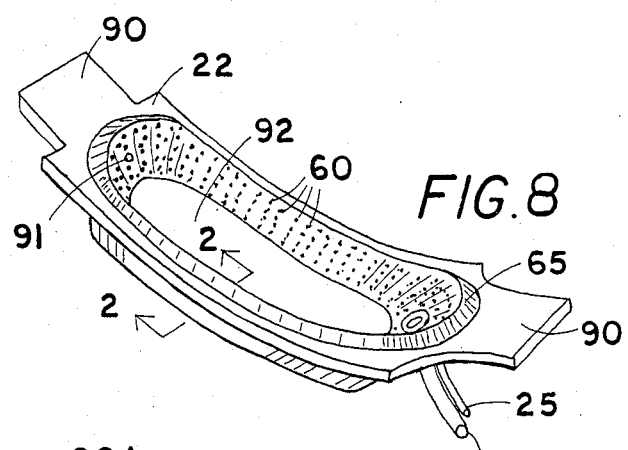
FIG. 8 is a perspective view of a collection vessel for women and babies.
Figure 9:
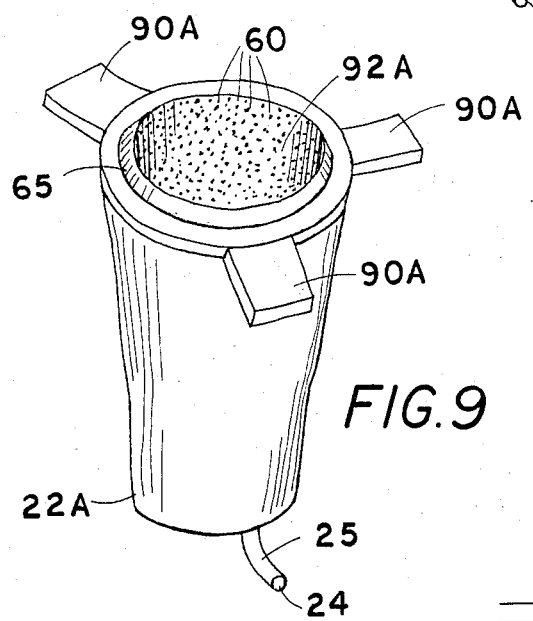
FIG. 9 is a perspective view of a collection vessel for adult males.

In FIGS. 1-3, 8 and 9, the collection vessel 22 is formed of a liquid impermeable material, such as soft silicon or other molded plastic, to provide an inexpensive and effective means for collecting the urine. The collection vessel 22 and 22A provides the minimal area necessary to conform to the genital-urinary area of the user. In FIG. 8 an elongated shallow well 92 collection vessel 22 is effective for female and young users. In FIG. 9 a collection vessel 22A with a deeper well 92A serves adult male users. Protruding tabs 90 and 90A from the top edges of the vessel are held against the body of the user by the elasticised belt 30 of FIG. 1. A resilient lip 65 is elevated above the tabs around the top edge of the well 92 and 92A. When the vacuum is applied through the flexible tube 24 leading from the collection vessel, the lip 65 is drawn tightly against the body of the user to form a liquid tight seal and prevent the escape of urine from the collection vessel. When there is no liquid in the vessel and consequently no vacuum the lip 65 is not sealed as tightly and air is allowed to circulate into the well 92 and 92A. An air vent 91 in the wall is adjustable by inserting different grommets.

Figure 5:
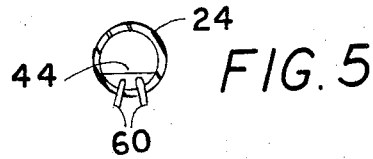
FIG. 5 is cross-sectional view taken through the flexible tube connecting the collection vessel to the storage tank showing a pair of electrical liquid sensors through the wall of the tube.

In FIGS. 2, 3, 8 and 9, a series of liquid sensors 60, 66 and 68 are spaced closely around the well 92 and 92A of the collection vessel 22. The spacing is sufficiently close that a small amount of liquid urine 44 is sufficient to stimulate the sensors. Pairs of electrical connectors 60 may be spaced very closely together in the vessel or in the flexible tube 24, as in FIG. 5, with the connectors wired in series through paired conductors 25 leading to a control, such as a solenoid, for activating a vacuum pump 43, all of which are wired in a series circuit with a power source 60. The power source should be a convertible system with D.C. batteries equipped with a self charging device and an alternate external D.C. plug 56 for vehicle cigarette lighter receptables and an A.C. plug 58 having a D.C. converter unit. Such devices are known in the art and will not be described in detail here. When a minimal amount of liquid urine 44 contacts both electrical connectors 60 the liquid completes the circuit to activate the vacuum pump 43 and maintain the pump in an active state until there is no longer any liquid between the sensors.

In FIG. 1 the paired conductors 25 are wired into a printed circuit board 48 which comprises standard electronic components to activate the vacuum pump 43. The vacuum pump 43 creates a vacuum in the tank 32 through a hollow conduit 38. A condensation collecting trap 46 in the conduit prevents liquid 44 in the tank from entering the pump 43. A filter 50, such as a charcoal filter, between the pump and outside serves a dual function of preventing urine odors from escaping the pump and of reducing the pump noise producing a quiet running system. The vacuum in the tank then draws through a one-way valve 36 and through flexible tube 24 on the collection vessel to pump the liquid urine 44 from the collection vessel into the storage tank 32 and then further serving to evaporate the remaining urine in the collection vessel area and on the body of the user until the sensor circuit connection is broken by the lack of liquid. The one-way valve 36 prevents liquid from reentering the flexible tube 24.

Figure 3:
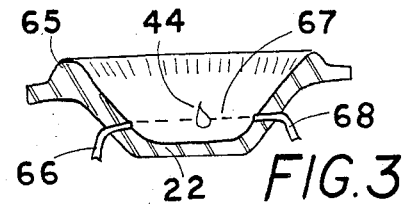
FIG. 3 is a cross-sectional view of a collection vessel having fibre optic liquid sensing means.
Figure 6:
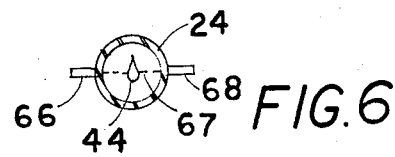
FIG. 6 is a cross-sectional view taken through the flexible tube showing a pair of fibre optic liquid sensors through the walal of the tube.

In FIGS. 3 and 6 an alternate liquid sensing means utilizes fibre optic elements 66 and 68 paired in optical alignment with a light beam 67 signal normally transmitted between the fibre optic elements. The elements may be closely spaced around the walls of the well in the collection vessel 22 or located in the flexible tube 24 as in FIG. 6. A small amount of liquid 44 will serve to interrupt the beam 67 and thereby cause a switch to activate the vacuum pump 43 as in the above example with the electrical connector sensors 60. No electrical current reaches the collection vessel 22 when using the fibre optic sensors 66 and 68. A very minimal amount of current (measured in milliamps) reaches the collection vessel 22 in the case of the electrical sensors 60. A ground fault as a fuse to break the circuit if too much current enters the system from outside when the system is plugged into an external power source.

Figure 10:
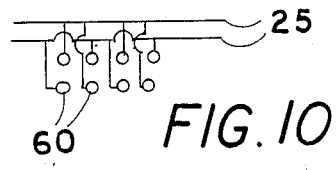
FIG. 10 is a schematic view of a grouping of liquid sensors.

In FIG. 10 a simplified diagram illustrates how electrical connector sensors 60 may be paired and any number of the pairs connected to a single pair of electrical conductors 25 to connect with the remainder of the circuit within the enclosure 20. Fibre optic elements may be ganged in the same fashion from a number of paired elements to a single pair.

The temporary storage tank 32, in FIG. 1, may be of any desired size, preferrably of sufficient depth ot hold from 24 to 48 hours of urine so that the tank need be emptied only once a day or once every two days, thereby requiring minimal effort. A liquid level sensor 42, working by the same principle as the liquid sensors in the collection vessel may be placed at any desired position in the tank to indicate when the tank reaches a desired level of fullness (preferably 75-80%). When the liquid reaches that level, the level sensor 42, wired in series with a buzzer 52 and a light 54 connected to the power source, will activate the signals to indicate that the tank should be emptied, thereby eliminating the problem of trying to calculate when the tank might be nearly full. A single indicator could be used if desired. Additional safety precautions include a rapid release valve 26 and 28 for emptying the tank quickly and another level sensor 40 located higher in the tank (preferrably 90% full) and below the vacuum conduit 38 and the flexible tube 24 from the collecting vessel. The second level sensor 40 would be wired into the control for the vacuum pump so that when the tank reached the 90% full mark, the level sensor 40 would automatically shut off the vacuum pump 43 and thereby prevent the tank from overflowing.

Automatic emptying of the collection vessel enables the use of a compact collection vessel which is inconspicuous and comfortable to wear even while walking. A quiet rotary vane vacuum pump housed in a simulated carrying case of backpack also provide inconspicuous elements so that the person with the problem may function normally. An automatic, safe and inconspicuous device for detecting, collecting and storing urine for urinary incontinent people of all ages, including youngsters of pre-toilet trained age, provides a welcome solution to the problems previously unsolved. Health, comfort and mobility are primary benefits derived from the invention described herein.

It is understood that the preceding description is given merely by way of illustration and not in limitation of the invention and that various modifications may be made thereto without departing from the spirit of the invention as claimed.

I claim:

1. An automatic in-place urine detecting, collecting and storing device for urinary incontinent users to maintain relative dryness adjacent to a user's body, wherein the device comprises;
   an elongated collection vessel approximately conforming to the user's urinary-genital area wherein the collection vessel comprises:
   an interior collection surface lining the collection vessel;
   a top edge which faces the user's body such that the interior collection surface surrounds the urinary-genital area upon putting the device on;
   an interior perimeter of the interior collection surface adjacent to the top edge immediately adjacent to the user's body;
   a resilient elevated lip which surrounds the top edge;
   a flexible tube leading from the collection vessel to a separate temporary storage tank having a level sensing means and a rapid release valve to empty the tank;
   a vacuum pump means for drawing the urine from the collection vessel through the flexible tube into the storage tank, wherein a one-way valve is positioned between the tube and the tank to prevent liquid flow from the tank into the tube, and wherein the vacuum draws the lip of the collection vessel into liquid tight contact with the body of the user;
   a multiplicity of droplet-sensitive liquid sensing means randomly located within the collection vessel which cover the interior collection surface of the collection vessel and cover the interior perimeter of the collection surface and can detect droplets of liquid when the device is in any spatial orientation which might cause urine to contact the body, wherein upon detecting liquid urine within the collection vessel, the liquid sensing means activates the vacuum pump to create a vacuum in the storage tank drawing the urine from the collection vessel to the storage tank until the sensor no longer detects liquid in the collection vessel leaving the collection vessel relatively dry.

2. The invention of claim 1 wherein the liquid sensing means comprises at least one pair of closely spaced low amperage electrical conductors wired in series with the vacuum pump, wherein liquid contacting both conductors simultaneously completes a circuit to activate the vacuum pump until the liquid no longer completes the circuit.

3. The invention of claim 1 wherein the liquid sensing means comprises at least one pair of fibre optic elements optically aligned with a beam of light passing between the pair of fibre optic elements and the fibre optic elements connect with a switching means for the vacuum so that liquid urine interrupting the beam will activate the vacuum pump to draw the liquid urine from the vessel until there is no liquid interrupting the beam.

4. The invention of claim 1 further comprising within the storage tank a sensing means to activate at least one signal when the liquid in the tank fills to a preselected level.

5. The invention of claim 1 further comprising within the storage tank a sensing means to deactivate the vacuum pump when the liquid in the tank fills to a preselected level.

6. The invention of claim 1 further comprising a condensation collection trap between the vacuum pump and the storage tank to prevent liquid from the storage tank entering the vacuum pump.

7. The invention of claim 1 further comprising an air filtering means between the vacuum pump and the outside exhaust to prevent urine odor from leaving the vacuum pump and muffle noise from the vacuum pump.

8. The invention of claim 1 wherein the collecting vessel is held in place against the body of the user by a supporting means around a portion of the user's body.

9. The invention of claim 1 wherein the vacuum pump is powered by an adaptable power source means which converts from a self-contained D.C. source, having a recharging means, to an external D.C. source or to an external A.C. source.

10. The invention of claim 1 wherein the collecting vessel is formed of flexible material shaped to fit users.

11. The invention of claim 1 further comprising an external casing provided with a handle and resembling a brief type case.

12. The invention of claim 1 further comprising an external casing provided with straps to fit over the shoulders of the user or over a portion of a structure supporting the user.

13. The invention of claim 1 further comprising a rapid release valve at the base of the storage tank for emptying the tank.

14. The invention of claim 1 wherein the liquid sensing means in the collecting vessel comprises a number of closely spaced low-amperage electrical contacts connected in a circuit to the vacuum pump so that a small amount of liquid between two electrical contacts completes the circuit to activate the vacuum pump until most of the liquid is removed from between the contacts to break the circuit, leaving the collecting vessel relatively dry.

15. The invention of claim 1 wherein the liquid sensing means in the collecting vessel comprises a number of closely spaced fibre optic elements paired in optical alignment within the collecting well, which fibre optic elements are connected to a control means for the vacuum pump, so that when any liquid interrupts the beam, the vacuum pump will be activated until liquid no longer interrupts the beam, leaving the collecting vessel relatively dry.

16. An automatic in-place urine detecting, collecting and storing device for urinary incontinent users to maintain relative dryness adjacent to a user's body, wherein the device comprises:
   an elongated liquid impervious collection vessel approximately conforming to the user's urinary-genital area, wherein the collection vessel comprises:
   an interior collection surface lining the collection vessel;
   a top edge which faces the user's body such that the interior collection surface surrounds the urinary-genital area upon putting the device on;
   an interior perimeter of the interior collection surface adjacent to the top edge immediately adjacent to the user's body;
   a resilient elevated lip which surrounds the top edge;

a temporary liquid storage tank distant from the collection vessel, wherein the storage tank comprises a liquid tight chamber having a capacity level sensing means to activate at least one signal means and a rapid release valve for emptying the tank;

a flexible tube leading from the collection vessel to the storage tank through a one-way valve which prevents flow from the tank to the collection vessel;

a vacuum pump means connected to the storage tank for drawing the urine from the collection vessel to the storage tank and drawing the lip of the collection vessel into liquid tight contact with the body of the user, which vacuum pump further acts to evaporate the liquid in the collection vessel by drawing on the collection vessel after the bulk of the liquid is removed therefrom;

a series of closely and randomly spaced droplet-sensitive liquid sensing means which cover the interior collection surface of the collection vessel and cover the interior perimeter of the collection surface, which liquid sensing means are connected to an activating means for the vacuum pump, so that a small amount of liquid in the collection vessel activates the vacuum pump when the device is in any spacial orientation which might cause urine to contact the body to draw and evaporate liquid from the collection vessel until the collection vessel is relatively dry.

17. An improvement in automatic in-place urine detecting, collecting and storing and evaporating devices for urinary incontinent users to maintain relative dryness adjacent to a user's body, wherein the device comprises:

an elongated liquid impervious collection vessel conforming to the user's urinary-genital area;

a temporary liquid storage tank distant from the collection vessel;

a flexible tube leading from the collection vessel to the storage tank;

a vacuum pump means connected to the storage tank for drawing the urine from the collection vessel to the storage tank, which vacuum pump further acts to evaporate the urine in the collection vessel until a state of relative dryness is produced inside the collection vessel adjacent to the user's skin;

a liquid sensing means capable of detecting very small amounts of liquid, wherein the liquid sensing means are connected to an activating means for the vacuum pump means to activate the vacuum pump until dryness is reached in the collection vessel; and wherein the improvements comprise positioning a series of closely and randomly spaced liquid sensing means which cover an interior collection surface of the collection vessel, including an interior perimeter of the collection surface adjacent to the user's body, to insure activation of the vacuum pump means when the device in any spacial orientation whenever any liquid is present in any location within the collection vessel which might cause the liquid to contact the body, whereby the vacuum pump further acts to evaporate the liquid in the collection vessel by drawing on the collection vessel after the bulk of the liquid is removed therefrom, thereby insuring relative dryness of the interior collection surface of the collection vessel and the skin of the user, for any bodily position of a user.

* * * * *